(12) United States Patent
Rosentreter et al.

(10) Patent No.: US 8,242,281 B2
(45) Date of Patent: Aug. 14, 2012

(54) SUBSTITUTED 2, 6-DIAMINO-3, 5-DICYANO-4-ARYLPYRIDINES AND THEIR USE AS ADENOSINE-RECEPTOR-SELECTIVE LIGANDS

(75) Inventors: Ulrich Rosentreter, Wuppertal (DE); Thomas Kramer, Wuppertal (DE); Andrea Vaupel, Riehen (CH); Walter Hubsch, Wuppertal (DE); Nicole Diedrichs, Wuppertal (DE); Thomas Krahn, Hagen (DE); Klaus Dembowsky, Boston, MA (US); Johannes-Peter Stasch, Solingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 598 days.

(21) Appl. No.: 11/607,262

(22) Filed: Dec. 1, 2006

(65) Prior Publication Data
US 2007/0213372 A1 Sep. 13, 2007

Related U.S. Application Data
(63) Continuation of application No. 10/471,072, filed as application No. PCT/EP02/01939 on Feb. 25, 2002, now abandoned.

(30) Foreign Application Priority Data
Mar. 7, 2001 (DE) .................................. 101 10 747

(51) Int. Cl.
*C07D 213/72* (2006.01)
*C07D 213/00* (2006.01)
*A01N 43/40* (2006.01)
(52) U.S. Cl. ......................... 546/307; 546/264; 514/344
(58) Field of Classification Search .................. 546/307, 546/264; 514/344
See application file for complete search history.

(56) References Cited

U.S. PATENT DOCUMENTS

| | | | |
|---|---|---|---|
| 5,889,002 A | 3/1999 | Nielsen et al. |
| 6,191,280 B1 | 2/2001 | Hamprecht et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,135,486 B1 | 11/2006 | Rosentreter et al. |
| 7,173,037 B2 | 2/2007 | Alonso-Alija et al. |
| 7,674,825 B2 | 3/2010 | Alonso-Alija et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,825,255 B2 | 11/2010 | Rosentreter et al. |
| 7,855,219 B2 | 12/2010 | Rosentreter et al. |

FOREIGN PATENT DOCUMENTS

| | | |
|---|---|---|
| EP | 0 608 565 A1 | 12/1993 |
| JP | 09-132529 | 5/1997 |
| JP | 10-324687 | 12/1998 |
| JP | 2003-183254 | 7/2003 |
| WO | 95/34563 | 12/1995 |
| WO | 99/03861 A1 | 1/1999 |
| WO | 02/48115 A2 | 6/2002 |
| WO | 02/50071 A1 | 6/2002 |

OTHER PUBLICATIONS

Hcaplus 1985:437345, "Reactivity of heterocyclic compounds. V. Behavior of 6-alkoxy-2-amino-(or chloro)-4-aryl-3,5-dicyanopyridines in the presence of nucleophiles", Quintela et. al.*
Patani et. al., "Bioisosterism: A Rational Approach in Drug Design", Chem. Rev. 96, 3147-3176, pp. 3147-3176.*
West, Anthony R., Solid State Chemistry and its Applications, Wiley, New York, 1988, pp. 358 & 365.*
Hcaplus 1985:437345, "Reactivity of heterocyclic compounds. V. Behavior of 6-alkoxy-2-amino-(or chloro)-4-aryl-3,5-dicyanopyridines in the presence of nucleophiles", Quintela et. al., 1984.*

(Continued)

*Primary Examiner* — Janet Andres
*Assistant Examiner* — Heidi Reese
(74) *Attorney, Agent, or Firm* — Thomas C. Blankinship; Karen B. King; William F. Gray

(57) ABSTRACT

The present invention relates to substituted 2,6-diamino-3,5-dicyano-4-arylpyridines of the formula (I)

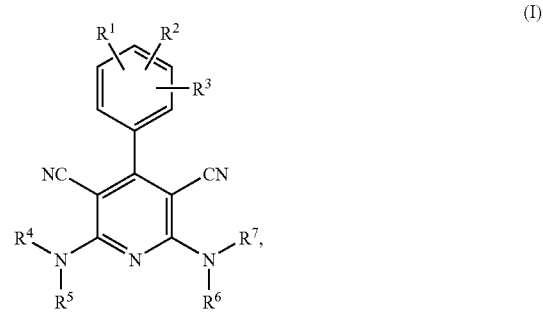

wherein the definitions of substituent groups $R^1$-$R^7$ are as provided in the specification and claims, to a pharmaceutical composition containing such a compound, to a process for preparation of such materials, and to their use as medicaments for the treatment of cardiovascular disorders and diabetes.

5 Claims, No Drawings

OTHER PUBLICATIONS

Patani et. al., "Bioisosterism: A Rational Approach in Drug Design", Chem. Rev. 96, pp. 3147-3176.*

Bauman A.E., "Updating the evidence that physical activity is good for health: an epidemiological review 2000-2003," J. Sci. Med. Sport, 7(1 Suppl):6-19 (2004 Apr.), abstract retrieved from MEDLINE Accession No. 2004312664, PubMed ID: 15214597.

Beukers M., Chang L., von Frijtag Drabbe Kuenzel J., Mulder-Krieger T., Spanjersberg R., Brussee J., lJzerman a., "New, Non-Adenosine, High-Potency Agonists for the Human Adenosine A2B Receptor with an Improved Selectivity Profile Compared to the Reference Agonist N-Ethylcarboxamidoadenosine", Journal of Medicinal Chemistry, 47 (15):3707-3709 (Jul. 2004).

Castedo L., Quintela J., Riguera R., "Synthesis and pharmacological activity of some nitrofuraldehyde cyanopyridine derivatives," Eur. J. Med. Chem., 19(6):555-557 (1984), abstract retrieved from CAPLUS Accession No. 1985:437337, EPO Document XP002202946.

Dyachenko V., Krivokolysko S., Sharanin Y., Litvinov V., "New Route to 6-Amino-4-aryl-3,5-dicyano-pyridine-2(1H)-thiones", Russian Journal of Organic Chemistry, 33(7):1014-1017 (1997).

Dyachenko V., Litvinov V., "Michael Reaction in SyntheSis of 6-Amino-4-(4-Butoxyphenyl)-3,5- Dicyanopyridine-2(1H)-thionene," Chemistry of Heterocyclic Compounds, 34(2):166-194 (1996).

Dyachenko, V., Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines, Russian Journal of General Chemistry, 76 (2):282-291 (2006).

Elnagdi M., Elghandour A., Ibrahim M., Hafiz I., "Studies with Polyfunctionally Substituted Heterocycles," Z. Naturforsch., 47b:572-578 (1992).

El-Torgoman A., El-Kousy S., "Nitriles in Heterocyclic Synthesis: The reaction of 2-Thiocarbamoyl Cinnamonitriles with Active Methylene Reagents", Z. Naturforsch., 42b:107-111 (1987).

Fuentes L., Vaquero J., Soto J. "Heterocycle synthesis. XVI. Reaction of malononitrile with benzylidenemalononitriles in presence of amines." An. Quim., Ser. C., 76(1): 68-69 (1980), English language abstract retrieved from Caplus Accession No. 1981:139574, EPO Document No. XP002202947.

Jacobson K., von Lubitz D., Daly J., Fredholm B., "Adenosine receptor ligands: differences with acute versus chronic treatment", Trends in Pharmacological Sciences, 17(3):108-113 (Mar. 1996), also retrieved as Caplus Accession No. 1996:257561.

Kambe S., Saito K., "Synthetic Studies Using a,β-Unsaturated Nitriles: Facile Synthesis of Pyridine Derivatives," Synthesis Communications, Jul. 1981, 531-533.

Klotz K.N., Hessling J., Helger J., Owman C., Kull B., Fredholm B.B., Lohse M.J., "Comparative pharmacology of human adenosine receptor subtypescharacterization of stably transfected receptors in CHO cells", Naunyn-Schmiedeberg's Arch Pharmacol 357:1-9 (1998).

Klotz, K., "Adenosine receptors and their ligands", Naunyn-Schmiedeberg's Arch. Pharmacol., 362:382-391 (2000), also retrieved as CAPLUS Accession No. 2000:814898 and EPO Document XP002520638.

Müller C., "Adenosine Receptor Ligands-Recent Developments Part I. Agonists", Current Medicinal Chemistry, 7:1269-1288 (2000).

Müller C., "Review. Cardiovascular & Renal. A1-Adenosine receptor antagonists," Exp. Opin. Ther. Patents, 7 (5):419-440 (1997).

Müller C., Stein B., "Adenosine Receptor Antagonists: Structures and Potential Therapeutic Applications", Current Pharmaceutical Design. 2:501-530 (1996).

Olah, M., Ren, H., Ostrowski, J., Jacobson, K., Stiles, G., "Cloning, Expression, and Characterization of the Unique Bovine A1 Adenosine Receptor", Journal of Biological Chemistry, 267(15):10764-10770 (May 1992).

Patani, G., LaVoie, E., "Bioisosterism: A Rational Approach in Drug Design", Chem. Rev., 96:3147-3176 (1996).

Pflueger A., Larson T.S., Nath K.A., King B.F., Gross J.M., Knox F.G., "Role of adenosine in contrast media-induced acute renal failure in diabetes mellitus." Mayo Clin Proc., 75(12):1275-83 (Dec. 2000), abstract retrieved from Medline Accession No. 2001070093, PubMed ID: 11126837.

Poulsen S.A., Quinn R., "Adenosine Receptors: New Opportunities for Future Drugs," Bioorganic & Medicinal Chemistry 6:619-641 (1998), EPO Document No. XP000985735.

Quintela J., Peinador C., Veiga M., Botana L., Alfonso A., Riguera R., "Synthesis, antihistaminic and cytotoxic activity of pyridothieno- and pyridodithienotriazines", Eur. J. Med. Chem. 33:887-897 (1998).

Quintela J., Soto J., "Reactivity of heterocyclic compounds. V. Behavior of 6-alkoxy-2-amino-(or chloro)-4-aryl-3,5-dicyanopyridines in the presence of nucleophiles," Anales de Quimica, Serie C: Quimica Organica y Bioquimica, 80(3):268-72 (1984), English language abstract retrieved from CAPLUS Accession No. 1985:437345, CAPLUS Document No. 103:37345, EPO Document No. XP002202945.

Rosenman R.N., "Do environmental effects on human emotions cause cardiovascular disorders?" Acta Physiologica Scandinavica, Supplement, 161/640 (133-136) (1997), abstract retrieved from EMBASE Accession No. 97358868.

Ruhe R.C., McDonald R.B., "Use of antioxidant nutrients in the prevention and treatment of type 2 diabetes," J. Am. Coll. Nutr., 20(5 Suppl):363S-369S, discussion 381S-383S (Oct. 2001), abstract retrived from Medline Accession No. 2001557411, PubMed Id: 11603645.

Shams H., Elkholy Y., Ibrahim N., Elnagdi M., "Nitriles in organic synthesis. New routes for synthesis of pyridines and azinothiopyrans," Journal fuer Praktische Chemie (Leipzig), 330(5):817-13 (1988), abstract retrieved from CAPLUS Accession No. 1989:497050.

Suttner S.W., Piper S.N., Boldt J., "The heart in the elderly critically ill patient," Curr. Opin. Crit. Care, 8(5):389-94 (Oct. 2002), abstract retrieved from MEDLINE Accession No. 2002495386, PubMed Id: 12357105.

Szydlowski W., Lopatynski J.,"Biological role of chromium," Diabetologia Polska, 10(3):365-370 (2003), English language abstract retrieved from EMBASE Accession No. 2004016455.

Velásquez E., "Chronic complications of polycystic ovary syndrome. Review.," Investisgacion Clinica, 43(3):205-13 (Sep. 2002), English language abstract retrieved from MEDLINE Accession No. 2002469511, PubMed Id: 12229282.

Vippagunta S., Brittain H., and Grant D., "Crystalline solids," Advanced Drug Delivery Reviews, 48(1):3-26 (May 2001).

West A., "Solid State Chemistry and its Applications," Wiley, New York, 1988, pp. 358 & 365.

Yu L., Reutzel S., Stephenson G., "Physical characterization of polymorphic drugs: an integrated characterization strategy," Pharmaceutical Science & Technology Today, 1(3):118-127 (Jun. 1998).

Avila, et al.: A1-, A2A- and A3-subtype adenosine receptors modulate intraocular pressure in the mouse, British Journal of Pharmacology, 2001, 134:241-245.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bundgaard:"Design of Prodrugs: Bioreversible derivatives for various functional groups and chemical entities," Elsevier Science Publishers B.V., 1985.

Cesar, et al.:"Triniethylsilyldiazomethane in the Preparation of Diazoketones via Mixed Anhydride and Coupling Reagent Methods: A New Approach to the Arndt—Eistert Synthesis," Tetrahedron Letters, 2001, 42: 7099-7102.

Crosson: Intraocular Pressure Responses to the Adenosine Agonist Cyclohexyladenosine: Evidence for a Dual Mechanism of Action, IOVS, Jul. 2001, 42(8): 1837-1840.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Guillory:"Generation of Polymorphs, Hydrates, Solvates, and Amorphouse Solids," in Polymorphism in Pharmaceutical Solids (Ed. Brittain), 1999, pp:183-226, Marcel Dekker, Inc.

Ibrahim, et al.:"Synthesis and Biological Activity of Some New Heterocyclic Quinoline Derivatives," Phosphorus, Sulfer, and Silicon, 1991, 57: 293-301.

Kambe, et al.:"Synthetic Studies Using a,β-Unsaturated Nitriles: Facile Synthesis of Pyridine Derivatives," Synthesis Communications, Jul. 1981, pp: 531-533.

Quintela, et al.:"Synthesis, Antihistaminic and Cytotoxic Activity of Pyridothieno- and Pyridodithienotriazines", Eur. J. Med. Chem, 1998, 33:887-897.

Ye, et al.:Organic Synthesis with α-Diazocarbonyl Compounds, Chem. Rev. 1994, 94:1091-1160.

U.S. Appl. No. 11/661,820, filed Mar. 10, 2008, published as US 2008-0269300.

U.S. Appl. No. 12/516,939, filed Nov. 24, 2009 published as US 2010-0069363.

U.S. Appl. No. 12/440,423, filed Dec. 23, 2009 published as US 2010-0093728.

U.S. Appl. No. 12/516,917, filed May 29, 2009, published as US 2010-0022544.

U.S. Appl. No. 12/671,019, filed Jan. 27, 2010, published as US 2011-0130377.

U.S. Appl. No. 12/671,694, filed Jul. 27, 2011, published as US 2011-0294718.

U.S. Appl. No. 12/922,172, filed May 16, 2011 published as US 2011-0207698.

U.S. Appl. No. 12/995,028, filed Feb. 16, 2011 published as US 2011-0207698.

U.S. Appl. No. 13/132,991, filed Aigist 23. 2011 published as US 2011-0294719.

U.S. Appl. No. 12/697,000, filed Jan. 29, 2010, published as US 2010-0197609.

U.S. Appl. No. 13/2010,889, filed Aug. 16, 2011.

* cited by examiner

SUBSTITUTED 2, 6-DIAMINO-3, 5-DICYANO-4-ARYLPYRIDINES AND THEIR USE AS ADENOSINE-RECEPTOR-SELECTIVE LIGANDS

The present invention relates to substituted 2,6-diamino-3,5-dicyano-4-arylpyridines, to a process for their preparation and to their use as medicaments.

Adenosine, a nucleoside consisting of adenine and D-ribose, is an endogenous factor having cell-protective activity, in particular under cell-damaging conditions with limited oxygen and substrate supply, such as, for example, in the case of ischemia in various organs (for example heart and brain).

Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to A1 or A3 receptors results in a decrease of the intracellular cAMP concentration via inhibition of adenylate cyclase.

According to the invention, "adenosine-receptor-selective ligands" are substances which bind selectively to one or more subtypes of the adenosine receptors, thus either mimicking the action of adenosine (adenosine agonists) or blocking its action (adenosine antagonists).

According to their receptor selectivity, adenosine-receptor-selective ligands can be divided into different categories, for example ligands which bind selectively to the A1 or A2 receptors of adenosine and in the case of the latter also, for example, those which bind selectively to the A2a or the A2b receptors of adenosine. Also possible are adenosine receptor ligands which bind selectively to a plurality of subtypes of the adenosine receptors, for example ligands which bind selectively to the A1 and the A2, but not to the A3 receptors of adenosine.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis." in J. Biol. Chem. 267 (1992) pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in Naunyn Schmiedebergs Arch. Pharmacol. 357 (1998) pages 1-9, the disclosure of which is hereby fully incorporated by way of reference).

The "adenosine-receptor-specific" ligands known from the prior art are mainly derivatives based on natural adenosine (S.-A. Poulsen and R. J. Quinn, "Adenosine receptors: new opportunities for future drugs" in Bioorganic and Medicinal Chemistry 6 (1998) pages 619-641; K. J. Broadley, "Drugs modulating adenosine receptors as potential therapeutic agents for cardiovascular diseases" in Exp. Opin. Ther. Patents 10 (2000) pages 1669-1692). However, most of the adenosine ligands known from the prior art have the disadvantage that their action is not really receptor-specific, that their activity is less than that of natural adenosine or that they have only very weak activity after oral administration. Thus they are mainly used only for experimental purposes.

It is an object of the present invention to find or provide pharmacologically active substances suitable for the prophylaxis and/or treatment of various disorders, in particular disorders of the cardiovascular system (cardiovascular disorders), the substances preferably acting as adenosine-receptor-selective ligands.

The present invention provides the use of compounds of the formula (I)

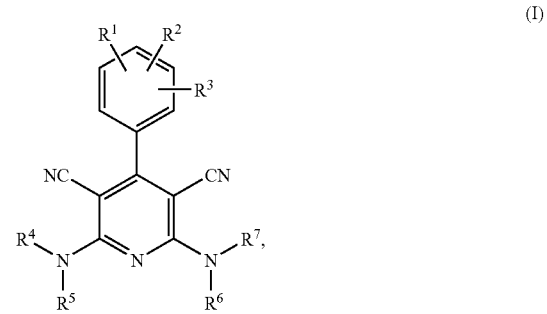

in which

R$^1$, R$^2$ and R$^3$ independently of one another are (C$_1$-C$_8$)-alkyl which may be substituted up to three times, independently of one another, by halogen, cyano, hydroxyl, amino, mono- or di-(C$_1$-C$_4$)-alkylamino, (C$_1$-C$_4$)-alkoxy, (C$_1$-C$_4$)-alkoxycarbonyl, (C$_3$-C$_7$)-cycloalkyl, (C$_2$-C$_4$)-alkenyl, (C$_2$-C$_4$)-alkynyl, —O—C(O)—R$^8$, (C$_6$-C$_{10}$)-aryl, 5- to 10-membered heteroaryl having up to three heteroatoms from the group consisting of N, O and/or S or (C$_6$-C$_{10}$)-aryloxy, (C$_6$-C$_{10}$)-aryl which may be substituted up to three times, independently of one another, by halogen, nitro, (C$_1$-C$_4$)-alkoxy, carboxyl, (C$_1$-C$_4$)-alkoxycarbonyl or mono- or di-(C$_1$-C$_4$)-alkylamino, (C$_1$-C$_8$)-alkoxy which may be substituted up to three times, independently of one another, by halogen, cyano, hydroxyl, amino, mono- or di-(C$_1$-C$_4$)-alkylamino, (C$_1$-C$_4$)-alkoxy, (C$_1$-C$_4$)-alkoxycarbonyl, (C$_3$-C$_7$)-cycloalkyl, (C$_2$-C$_4$)-alkenyl, (C$_2$-C$_4$)-alkynyl, —O—C(O)—R$^8$, (C$_6$-C$_{10}$)-aryl, 5- to 10-membered heteroaryl having up to three heteroatoms from the group consisting of N, O and/or S or $(C_6-C_{10})$-aryloxy, hydrogen, hydroxyl, halogen, nitro, cyano or —NH—C(O)—$R^9$, in which $R^8$ and $R^9$ independently of one another represent $(C_1-C_8)$-alkyl which may be substituted by hydroxyl or $(C_1-C_4)$-alkoxy, $(C_3-C_7)$-cycloalkyl or $(C_6-C_{10})$-aryl which for its part may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, or $R^1$ and $R^2$ are attached to adjacent phenyl ring atoms and together with the two ring carbon atoms form a 5- to 7-membered saturated or partially unsaturated heterocycle having one or two heteroatoms from the group consisting of N, O and/or S, which heterocycle may be substituted by $(C_1-C_4)$-alkyl or oxo, $R^4$ represents hydrogen, $(C_1-C_8)$-alkyl which may be substituted up to three times, independently of one another, by hydroxyl, $(C_1-C_4)$-alkoxy, $(C_3-C_7)$-cycloalkyl, $(C_6-C_{10})$-aryl or 5- to 6-membered heteroaryl having up to three heteroatoms from the group consisting of N, O and/or S, or $(C_3-C_8)$-cycloalkyl which for its part may be substituted by hydroxyl or $(C_1-C_6)$-alkyl, $R^5$ represents hydrogen or $(C_1-C_4)$-alkyl which may be substituted by hydroxyl, $(C_1-C_4)$-alkoxy or $(C_3-C_7)$-cycloalkyl, or $R^4$ and $R^5$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, $R^6$ represents $(C_3-C_7)$-cycloalkyl or $(C_1-C_8)$-alkyl, where alkyl may be substituted by $(C_3-C_7)$-cycloalkyl, hydroxyl, $(C_1-C_4)$-alkoxy, $(C_2-C_4)$-alkenyl, $(C_2-C_4)$-alkynyl, $(C_6-C_{10})$-aryl or 5- to 10-membered heteroaryl having up to three heteroatoms from the group consisting of N, O and/or S, where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano or hydroxyl, and $R^7$ represents hydrogen or $(C_1-C_4)$-alkyl which may be substituted by hydroxyl, $(C_1-C_4)$-alkoxy or $(C_3-C_7)$-cycloalkyl, or $R^6$ and $R^7$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, and their salts, hydrates, hydrates of the salts and solvates for the prophylaxis and/or treatment of disorders.

Some of the substances mentioned above which can be used according to the present invention for the prophylaxis and/or treatment of disorders are known from the literature (see Quintela et al., Anales de Quimica 80, pages 268-272, (1984); Fuentes et al., Anales de Quimica 76, pages 68-69, (1980). However, a therapeutical application of the known compounds has hitherto not been described in the literature. For the first time, this is done in the context of the present invention.

Depending on the substitution pattern, the compounds of the formula (I) can exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components. Likewise, the present invention also relates to the other tautomers of the compounds of the formula (I) and their salts.

Salts of the compounds of the formula (I) can be physiologically acceptable salts of the compounds according to the invention with mineral acids, carboxylic acids, or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, trifluoroacetic acid, acetic acid, propionic acid, lactic acid, tartaric acid, citric acid, fumaric acid, maleic acid or benzoic acid.

Salts which may be mentioned include salts with customary bases, such as, for example, alkali metal salts (for example sodium salts or potassium salts), alkaline earth metal salts (for example calcium salts or magnesium salts) or ammonium salts, derived from ammonia or organic amines, such as, for example, diethylamine, triethylamine, ethyldiisopropylamine, procaine, dibenzylamine, N-methyl-morpholine, dihydroabietylamine, 1-ephenamine or methylpiperidine.

According to the invention, hydrates or solvates are those forms of the compounds of the formula (I) which, in solid or liquid state, form, by hydration with water or coordination with solvent molecules, a molecule compound or a complex. Examples of hydrates are sesquihydrates, monohydrates, dihydrates or trihydrates. Likewise, the hydrates or solvates of salts of the compounds according to the invention are also suitable.

Moreover, the invention also includes prodrugs of the compounds according to the invention. According to the invention, prodrugs are forms of compounds of the formula (I) which for their part may be biologically active or inactive, but which can be converted under physiological conditions (for example metabolically or solvolytically) into the corresponding biologically active form.

In the context of the present invention, the substituents have, unless defined otherwise, the following meanings:

Halogen generally represents fluorine, chlorine, bromine or iodine. Preference is given to fluorine, chlorine or bromine. Very particularly preferred are fluorine or chlorine.

$(C_1-C_8)$-Alkyl, $(C_1-C_6)$-alkyl and $(C_1-C_4)$-alkyl generally represent a straight-chain or branched alkyl radical having 1 to 8, 1 to 6 and 1 to 4 carbon atoms, respectively.

Preference is given to a straight-chain or branched alkyl radical having 1 to 6 carbon atoms. Particular preference is given to a straight-chain or branched alkyl radical having 1 to 4 carbon atoms. Examples which may be mentioned are: methyl, ethyl, n-propyl, isopropyl, n-butyl, sec-butyl, isobutyl and tert-butyl.

$(C_2-C_4)$-Alkenyl generally represents a straight-chain or branched alkyl radical having 2 to 4 carbon atoms. Examples which may be mentioned are: vinyl, allyl, isopropenyl and n-but-2-en-1-yl.

(C₂-C₄)-Alkynyl generally represents a straight-chain or branched alkynyl radical having 2 to 4 carbon atoms. Examples which may be mentioned are: ethynyl, n-prop-2-yn-1-yl and n-but-2-yn-1-yl.

(C₁-C₈)-Alkoxy, (C₁-C₆)-alkoxy and (C₁-C₄)alkoxy generally represent a straight-chain or branched alkoxy radical having 1 to 8, 1 to 6 and 1 to 4 carbon atoms, respectively. Preference is given to a straight-chain or branched alkoxy radical having 1 to 6 carbon atoms. Particular preference is given to a straight-chain or branched alkoxy radical having 1 to 4 carbon atoms. Examples which may be mentioned are: methoxy, ethoxy, n-propoxy, isopropoxy, n-butoxy, isobutoxy, sec-butoxy, tert-butoxy.

(C₁-C₄)-Alkoxycarbonyl generally represents a straight-chain or branched alkoxy radical having 1 to 4 carbon atoms which is attached via a carbonyl group. Examples which may be mentioned are: methoxycarbonyl, ethoxycarbonyl, n-propoxycarbonyl, isopropoxycarbonyl and t-butoxycarbonyl.

In the context of the invention, mono- or di-(C₁-C₄)-alkylamino represents an amino group having one or two identical or different straight-chain or branched alkyl substituents each having 1 to 4 carbon atoms. Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

(C₃-C₇)-Cycloalkyl and (C₃-C₆)-cycloalkyl generally represent a cyclic alkyl radical having 3 to 7 and 3 to 6 carbon atoms, respectively. Preference is given to cyclic alkyl radicals having 3 to 6 carbon atoms. Examples which may be mentioned are: cyclopropyl, cyclobutyl, cyclopentyl or cyclohexyl.

(C₆-C₁₀)-Aryl generally represents an aromatic radical having 6 to 10 carbon atoms. Preferred aryl radicals are phenyl and naphthyl.

(C₆₋₁₀)-Aryloxy generally represents an aromatic radical as defined above which is attached via an oxygen atom.

5- to 10-membered heteroaryl having up to 3 heteroatoms from the group consisting of N, O and/or S generally represents a mono- or bicyclic, optionally benzo-fused heteroaromatic which is attached via a ring carbon atom of the heteroaromatic, if appropriate also via a ring nitrogen atom of the heteroaromatic. Examples which may be mentioned are: pyridyl, pyrimidyl, pyridazinyl, pyrazinyl, thienyl, furyl, pyrrolyl, pyrazolyl, imidazolyl, triazolyl, thiazolyl, oxazolyl, oxdiazolyl, isoxazolyl, benzofuranyl, benzothienyl or benzimidazolyl. The corresponding heteroaromatics having fewer heteroatoms, such as, for example, those having one or 2 heteroatoms from the group consisting of N, O and/or S, or those having a smaller ring size, such as, for example, 5- or 6-membered heteroaryl, are derived analogously from this definition. In general, preference is given to 5- or 6-membered aromatic heterocycles having one or 2 heteroatoms from the group consisting of N, O and/or S. Examples which may be mentioned are: pyridyl, pyrimidyl, pyridazinyl, furyl, imidazolyl or thienyl.

5- to 7-membered heterocycle generally represents a saturated or partially unsaturated, optionally benzo-fused heterocycle having up to 3 heteroatoms from the group consisting of N, O and/or S. Examples which may be mentioned are: tetrahydrofuryl, pyrrolidinyl, pyrrolinyl, dihydropyridinyl, piperidinyl, piperazinyl, morpholinyl, thiomorpholinyl, hexahydropyranyl. The corresponding heterocycles having fewer heteroatoms, such as, for example, one or 2 heteroatoms from the group consisting of N, O and/or S, or a smaller ring size, such as, for example, 5- or 6-membered heterocyclyl, are derived analogously from this definition. Preference is given to saturated heterocycles having up to 2 heteroatoms from the group consisting of N, O and/or S, in particular piperidinyl, piperazinyl, morpholinyl and pyrrolidinyl.

Moreover, the present invention relates to novel compounds of the formula (I)

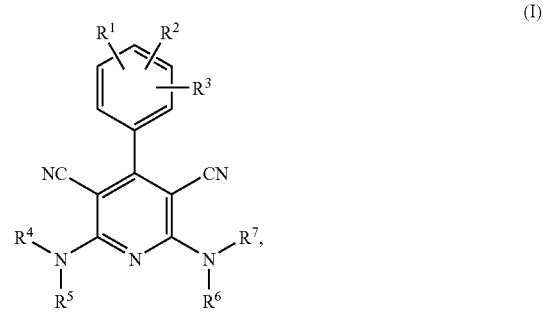

in which
R¹, R² and R³ independently of one another are (C₁-C₈)-alkyl which may be substituted up to three times, independently of one another, by halogen, cyano, hydroxyl, amino, mono- or di-(C₁-C₄)-alkylamino, (C₁-C₄)-alkoxy, (C₁-C₄)-alkoxycarbonyl, (C₃-C₇)-cycloalkyl, (C₂-C₄)-alkenyl, (C₂-C₄)-alkynyl, —O—C(O)—R⁸, (C₆-C₁₀)-aryl, 5- to 10-membered heteroaryl having up to three heteroatoms from the group consisting of N, O and/or S or (C₆-C₁₀)-aryloxy, (C₆-C₁₀)-aryl which may be substituted up to three times, independently of one another, by halogen, nitro, (C₁-C₄)-alkoxy, carboxyl, (C₁-C₄)-alkoxycarbonyl or mono- or di-(C₁-C₄)-alkylamino, (C₁-C₈)-alkoxy which may be substituted up to three times, independently of one another, by halogen, cyano, hydroxyl, amino, mono- or di-(C₁-C₄)-alkylamino, (C₁-C₄)-alkoxy, (C₁-C₄)-alkoxycarbonyl, (C₃-C₇)-cycloalkyl, (C₂-C₄)-alkenyl, (C₂-C₄)-alkynyl, —O—C(O)—R⁸, (C₆-C₁₀)-aryl, 5- to 10-membered heteroaryl having up to three heteroatoms from the group consisting of N, O and/or S or (C₆-C₁₀)-aryloxy, hydrogen, hydroxyl, halogen, nitro, cyano or —NH—C(O)—R⁹, in which
R⁸ and R⁹ independently of one another represent (C₁-C₈)-alkyl which may be substituted by hydroxyl or (C₁-C₄)-alkoxy, (C₃-C₇)-cycloalkyl or (C₆-C₁₀)-aryl which for its part may be substituted up to three times, independently of one another, by halogen, nitro, (C₁-C₄)-alkoxy, carboxyl, (C₁-C₄)-alkoxycarbonyl or mono- or di-(C₁-C₄)-alkylamino, or R¹ and R² are attached to adjacent phenyl ring atoms and together with the two ring carbon atoms form a 5- to 7-membered saturated or partially unsaturated heterocycle having one or two heteroatoms from the group consisting of N, O and/or S, which heterocycle may be substituted by (C₁-C₄)-alkyl or oxo, R⁴ represents hydrogen, (C₁-C₈)-alkyl which may be substituted up to three times, independently of one another, by hydroxyl, (C₁-C₄)-alkoxy, (C₃-C₇)-cycloalkyl, (C₆-C₁₀)-aryl or 5- to 6-membered heteroaryl having up to three heteroatoms from the group consisting of N, O and/or S, or $(C_3-C_8)$-cycloalkyl which for its part may be substituted by hydroxyl or $(C_1-C_6)$-alkyl, $R^5$ represents hydrogen or $(C_1-C_4)$-alkyl which may be substituted by hydroxyl, $(C_1-C_4)$-alkoxy or $(C_3-C_7)$-cycloalkyl, or $R^4$ and $R^5$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, $R^6$ represents $(C_3-C_7)$-cycloalkyl or $(C_1-C_8)$-alkyl, where alkyl may be substituted by $(C_3-C_7)$-cycloalkyl, hydroxyl, $(C_1-C_4)$-alkoxy, $(C_2-C_4)$-alkenyl, $(C_2-C_4)$-alkynyl, $(C_6-C_{10})$-aryl or 5- to 10-membered heteroaryl having up to three heteroatoms from the group consisting of N, O and/or S, where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano or hydroxyl, and $R^7$ represents hydrogen or $(C_1-C_4)$-alkyl which may be substituted by hydroxyl, $(C_1-C_4)$-alkoxy or $(C_3-C_7)$-cycloalkyl, or $R^6$ and $R^7$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, and their salts, hydrates, hydrates of the salts and solvates, except for the following compounds of the formula (I) in which the radicals $R^1$, $R^2$, $R^3$, $R^4$, $R^5$, $R^6$ and $R^7$ are as defined below:

$R^1=R^2=R^3=R^5=R^7=H$; $R^4=R^6=$2-hydroxyethyl
$R^1=R^2=R^3=R^5=R^7=H$; $R^4=R^6=$benzyl
$R^1=R^2=R^3=R^5=R^7=H$; $R^4=R^6=$n-butyl Preference is given to compounds of the formula (I) in which $R^1$, $R^2$ and $R^3$ independently of one another are hydrogen, hydroxyl, $(C_1-C_6)$-alkyl, trifluoromethyl, trifluoromethoxy, fluorine, chlorine, nitro, $(C_1-C_4)$-alkoxy which may be substituted by hydroxyl, $(C_1-C_4)$-alkoxy, —O—C(O)—$CH_3$, —O—C(O)—$C_2H_5$, $(C_3-C_7)$-cycloalkyl or $(C_2-C_4)$-alkenyl, —NH—C(O)—$CH_3$ or —NH—C(O)—$C_2H_5$, or $R^1$ and $R^2$ are attached to adjacent phenyl ring atoms and represent a group —O—$CH_2$—O— or —O—$CH_2$—$CH_2$—O—, $R^4$ represents hydrogen or $(C_1-C_4)$-alkyl which may be substituted by phenyl, pyridyl, $(C_1-C_4)$-alkoxy or mono- or disubstituted by hydroxyl, $R^5$ represents hydrogen, $R^6$ represents $(C_3-C_7)$-cycloalkyl or $(C_1-C_6)$-alkyl which may be substituted up to two times, independently of one another, by hydroxyl, $(C_1-C_4)$-alkoxy, $(C_3-C_7)$-cycloalkyl, phenyl or 5- or 6-membered heterocyclyl having up to three heteroatoms from the group consisting of N, O and/or S, where phenyl and heteroaryl for their part may be substituted by fluorine, chlorine, $(C_1-C_4)$-alkyl, $(C_1-C_4)$-alkoxy, amino, mono- or di-$(C_1-C_4)$-alkylamino, nitro, cyano or hydroxyl, $R^7$ represents hydrogen and their salts, hydrates, hydrates of the salts and solvates, except for the following compounds of the formula (I) in which the radicals $R^1$, $R^2$, $R^3$, $R^4$, $R^5$, $R^6$ and $R^7$ are as defined below:

$R^1=R^2=R^3=R^5=R^7=H$; $R^4=R^6=$2-hydroxyethyl
$R^1=R^2=R^3=R^5=R^7=H$; $R^4=R^6=$benzyl
$R^1=R^2=R^3=R^5=R^7=H$; $R^4=R^6=$n-butyl Particular preference is given to compounds of the formula (I)

in which $R^1$ represents hydrogen, hydroxyl, chlorine, nitro, methyl, methoxy, ethoxy, n-propoxy, isopropoxy, n-butoxy or —NH—C(O)—$CH_3$, where the alkoxy radicals for their part may be substituted by hydroxyl, methoxy, ethoxy, n-propoxy, isopropoxy, n-butoxy, —O—C(O)—$CH_3$ or cyclopropyl, $R^2$ and $R^3$ represent hydrogen, $R^4$ represents hydrogen, methyl, ethyl, n-propyl or isopropyl, where the alkyl radicals for their part may be substituted by pyridyl, methoxy, ethoxy, n-propoxy, isopropoxy, n-butoxy or mono- or disubstituted by hydroxyl, $R^5$ represents hydrogen, $R^6$ represents methyl, ethyl n-propyl, isopropyl, where the alkyl radicals for their part may be mono- or disubstituted, independently of one another, by cyclopropyl, phenyl which for its part may be substituted by fluorine, trifluoromethyl or methoxy, pyridyl, furyl, thienyl, benzimidazolyl, pyrrolidinonyl, N-methylpyrrolidinonyl, N-methylpyrrolidinyl, N-ethylpyrrolidinyl, N-methylimidazolidinonyl, or cyclopropyl and $R^7$ represents hydrogen and their salts, hydrates, hydrates of the salts and solvates.

The general or preferred radical definitions or illustrations given above can be combined with one another if desired, i.e. including combinations between the respective ranges and preferred ranges. They apply both to the end products and, correspondingly, to precursors and intermediates.

The present invention furthermore relates to a process for preparing compounds of the formula (I), characterized in that compounds of the formula (II)

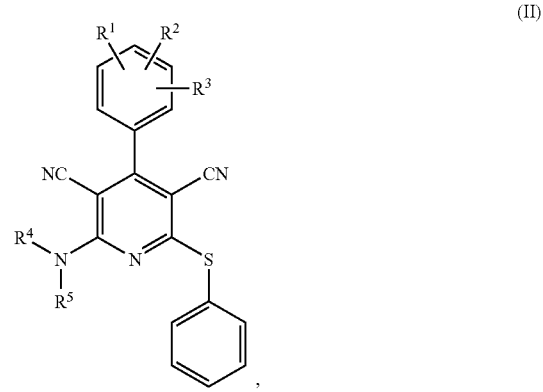

(II)

in which $R^1$, $R^2$, $R^3$, $R^4$ and $R^5$ are as defined above, are reacted in a solvent with compounds of the formula (III)

$R^6$—NH—$R^7$ (III)

in which

R⁶ and R⁷ are as defined above.

The process according to the invention can be illustrated in an exemplary manner by the formula scheme below:

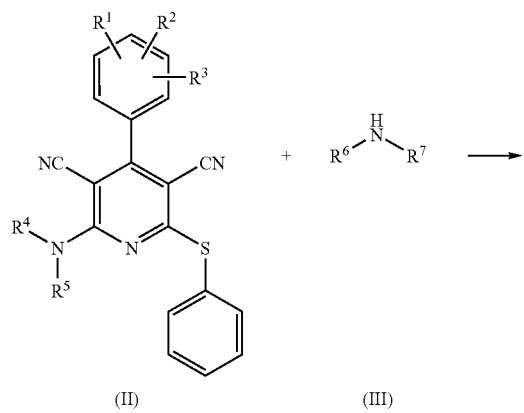

(II)          (III)

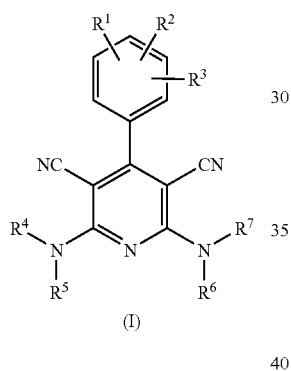

(I)

Suitable solvents for the process according to the invention are organic solvents which do not change under the reaction conditions. These include alcohols, such as methanol, ethanol and isopropanol, ketones, such as acetone and methyl ethyl ketone, acyclic and cyclic ethers, such as diethyl ether and tetrahydrofuran, esters, such as ethyl acetate, butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). Another suitable solvent is water. It is also possible to use mixtures of the solvents mentioned above. Preference is given to dimethylformamide.

The reaction is generally carried out in a ratio of from 2 to 8 mol of the compound (III) per mole of the compound (II).

The reaction is generally carried out in a temperature range of from −78° C. to +180° C., preferably in a range of from +20° C. to +160° C., in particular at from +80 to +130° C.

The reaction can be carried out under atmospheric, elevated or reduced pressure (for example in the range of from 0.5 to 5 bar). In general, the reaction is carried out under atmospheric pressure.

Compounds of the formula (II) in which $R^4$ equals $R^5$ equals hydrogen are known to the person skilled in the art or can be prepared by customary methods known from the literature [i.e., for example, Kambe et al., Synthesis 1981, pages 531-533; Elnagdi et al., Z. Naturforsch. 47b, pages 572-578, (1991)]

Compounds of the formula (II) in which $R^4$ and/or $R^5$ are not hydrogen can be prepared by converting compounds of the formula (IV)

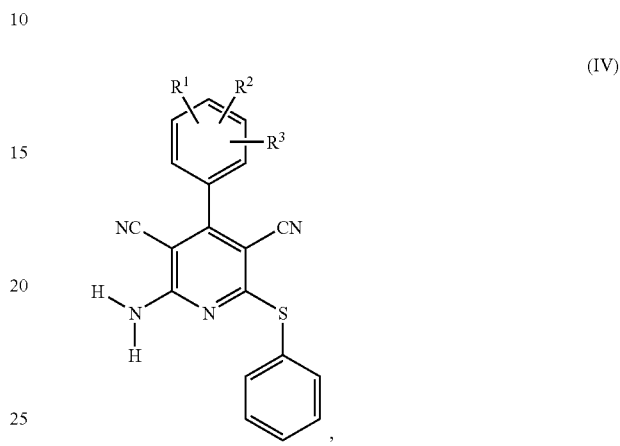

in which $R^1$, $R^2$ and $R^3$ are as defined above, with copper(II) chloride and isoamyl nitrite in a suitable solvent into compounds of the formula (V)

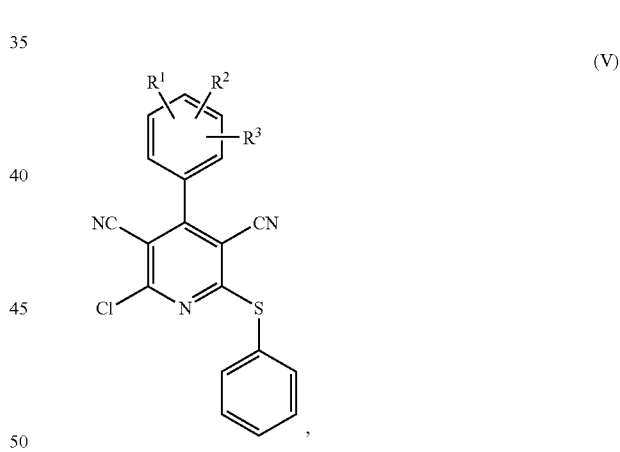

in which $R^1$, $R^1$ and $R^3$ are as defined above, and then reacting these with compounds of the formula (VI)

in which $R^4$ and $R^5$ are as defined above to give compounds of the formula (II).

The preparation of compounds of the formula (II) can be illustrated in an exemplary manner by the formula scheme below:

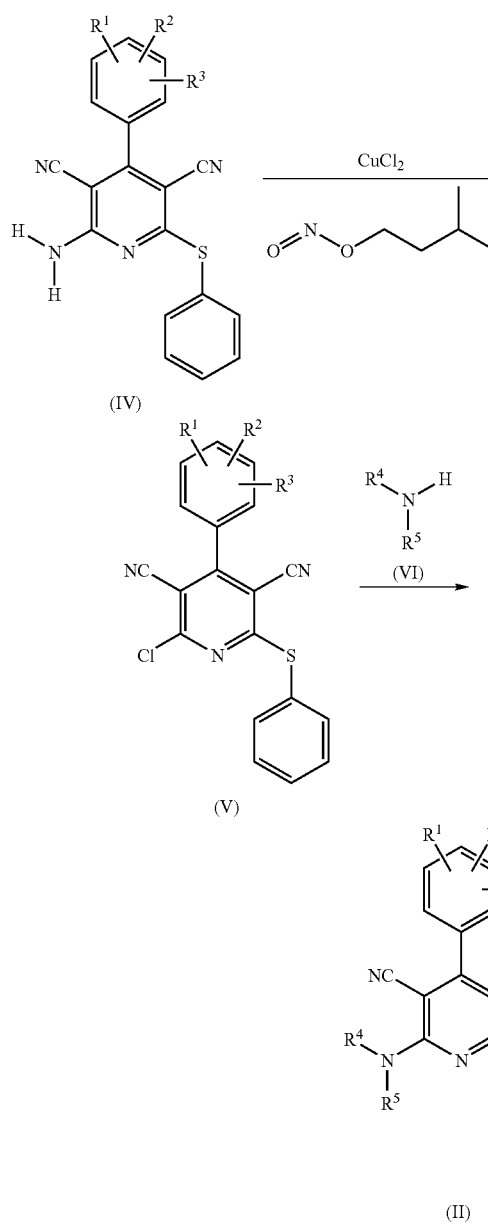

The process step (IV)→(V) is generally carried out using a molar ratio of from 2 to 12 mol of copper(II) chloride and from 2 to 12 mol of isoamyl nitrite per mole of (IV).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile or pyridine. It is also possible to use mixtures of the solvents mentioned above. Preferred solvents are acetonitrile and dimethylformamide.

The reaction is generally carried out in a temperature range of from −78° C. to +180° C., preferably in the range of from +20° C. to +100IC, in particular at from +20 to +60° C.

The reaction can be carried out at atmospheric, elevated or reduced pressure (for example in the range of from 0.5 to 5 bar). In general, the reaction is carried out at atmospheric pressure.

The process step (V)+(VI)→(II) is generally carried out using a molar ratio of from 1 to 8 mol of (VI) per mole of (V).

Suitable solvents are all organic solvents which are inert under the reaction conditions. These include alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). Another suitable solvent is water. It is also possible to use mixtures of the solvents mentioned above. The preferred solvent is dimethylformamide.

The reaction is generally carried out in a temperature range of from −78° C. to +180° C., preferably in the range of from +20° C. to +160° C., in particular at from +20 to +40° C.

The reaction can be carried out at atmospheric, elevated or reduced pressure (for example in the range of from 0.5 to 5 bar). In general, the reaction is carried out at atmospheric pressure.

Compounds of the formula (IV) are known to the person skilled in the art or can be prepared by customary methods known from the literature. Reference may be made, in particular, to the following publications, the respective content of which is expressly incorporated herein by way of reference:

Kambe et al., Synthesis 1981, pages 531-533

Elnagdi et al., Z. Naturforsch. 47b, pages 572-578, (1991)

The compounds of the general formulae (III) and (VI) are either commercially available, known to the person skilled in the art or can be prepared by customary methods.

Surprisingly, the compounds of the formula (I) have an unforeseeable useful pharmacological activity spectrum and are therefore suitable in particular for the prophylaxis and/or treatment of disorders.

The compounds of the formula (I) are suitable for the prophylaxis and/or treatment of a number of disorders, such as, for example, in particular disorders of the cardiovascular system (cardiovascular disorders).

In the context of the present invention, cardiovascular disorders are to be understood as meaning, in particular, for example the following disorders: coronary heart disease, hypertension (high blood pressure), restenosis after balloon dilation of peripheral blood vessels, arteriosclerosis, tachycardia, arrhythmias, peripheral vascular disorders and cardiovascular disorders, stable and unstable angina pectoris and atrial fibrillation.

The compounds of the formula (I) are furthermore also particularly suitable, for example, for reducing the size of the myocardial area affected by an infarct.

The compounds of the formula (I) are furthermore particularly suitable, for example, for the prophylaxis and/or treatment of thromboembolic disorders and ischemias, such as myocardial infarction, stroke and transitory ischemic attacks.

Finally, the compounds of the formula (I) are in particular also suitable, for example, for the prophylaxis and/or treatment of diabetes, in particular diabetes mellitus.

The present invention also relates to the use of the compounds of the formula (I) for preparing medicaments and pharmaceutical compositions for the prophylaxis and/or treatment of the clinical pictures mentioned above.

The present invention furthermore relates to a method for the prophylaxis and/or treatment of the clinical pictures mentioned above using the compounds of the formula (I).

The pharmaceutical activity of the compounds of the formula (I) mentioned above can be explained in particular by their action as selective ligands on A1 adenosine receptors.

In the context of the present invention, adenosine receptor ligands are referred to as being "selective" if, firstly, they are clearly active on one or more adenosine receptor subtypes and, secondly, the activity that can be observed on one or more other adenosine receptor subtypes is considerably weaker, if present at all, where, with respect to the test methods for selectivity of action, reference is made to the test methods described in Section A. II.

One advantage of the compounds of the formula (I) according to the invention is that they are more selective than adenosine receptor ligands of the prior art.

The receptor selectivity can be determined by biochemical measurement of the intracellular messenger cAMP in the transfected cells which specifically only express one subtype of the adenosine receptors. In the case of A1 agonists (coupling preferably via Gi proteins) a decrease of the intracellular cAMP content is noticed under conditions in which the intracellular cAMP concentration would be significantly increased by stimulating adenylate cyclase. In contrast, in the case of A1 antagonists, an increase of the intracellular cAMP concentration is observed after comparable prestimulation of adenylate cyclase plus stimulation with adenosine or adenosine-like substances.

Thus, compounds of the formula (I) which bind selectively to adenosine A1 receptors are preferably suitable for myocard protection and for the prophylaxis and/or treatment of tachycardia, atrial arrhythmia, cardiac insufficiency, myocardial infarction, acute kidney failure, diabetes, pain and for wound healing.

The subject matter of the present invention furthermore includes medicaments and pharmaceutical compositions comprising at least one compound of the formula (I), preferably together with one or more pharmacologically acceptable auxiliaries or carriers, and their use for the purposes mentioned above.

Suitable for administering the compounds of the formula (I) are all customary administration forms, i.e. oral, parenteral, inhalative, nasal, sublingual, rectal, local, such as, for example, in the case of implants or stents, or external, such as, for example, transdermal. In the case of parenteral administration, particular mention may be made of intravenous, intramuscular and subcutaneous administration, for example as a subcutaneous depot. Particular preference is given to oral administration.

Here, the active compounds can be administered on their own or in the form of preparations. Suitable preparations for oral administration are inter alia tablets, capsules, pellets, sugar-coated tablets, pills, granules, solid and liquid aerosols, syrups, emulsions, suspensions and solutions. Here, the active compound has to be present in such a quantity that a therapeutic effect is obtained. In general, the active compound can be present in a concentration of from 0.1 to 100% by weight, in particular from 0.5 to 90% by weight, preferably from 5 to 80% by weight, i.e. the active compound should be present in quantities sufficient to achieve the dosage range mentioned.

To this end, the active compounds can be converted in a manner known per se to the customary preparations. This is achieved using inert nontoxic pharmaceutically suitable carriers, auxiliaries, solvents, vehicles, emulsifiers and/or dispersants.

Auxiliaries which may be mentioned are, for example: water, nontoxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugars (for example lactose), emulsifiers, dispersants (for example polyvinylpyrrolidone) and glidants (for example magnesium sulfate).

In the case of oral administration, tablets may, of course, also contain additives such as sodium citrate, together with adjuvants such as starch, gelatin and the like. Aqueous preparations for oral administration may furthermore be admixed with flavor enhancers or colorants.

In general, it has been found to be advantageous to administer, in the case of parenteral administration, quantities of from about 0.1 to about 10 000 µg/kg, preferably from about 1 to about 1000 µg/kg, in particular from about 1 µg/kg to about 100 µg/kg, of body weight, to obtain effective results. In the case of oral administration, the quantity is from about 0.1 to about 10 mg/kg, preferably from about 0.5 to about 5 mg/kg, in particular from about 1 to about 4 mg/kg, of body weight.

In spite of this, it may still be required, depending on body weight, administration route, individual response to the active compound, the type of preparation and the time or interval at which administration takes place, to deviate from the quantities mentioned.

The present invention is illustrated by the following examples, which do not restrict the invention in any way.

A. ASSESSING PHYSIOLOGICAL ACTIVITY

I. Detecting the Cardiovascular Effect

Langendorff Heart of the Rat:

After the thorax has been opened, the heart is rapidly removed from anesthetized rats and introduced into a conventional Langendorff apparatus. The coronary arteries are perfused at constant volume (10 ml/min), and the resulting perfusion pressure is recorded by way of an appropriate pressure sensor. In this set-up, a decrease in the perfusion pressure corresponds to a relaxation of the coronary arteries. At the same time, the pressure which the heart develops during each contraction is measured by way of a balloon, which has been introduced into the left ventricle, and a second pressure sensor. The frequency of the heart, which is beating in isolation, is calculated from the number of contractions per time unit.

II. Assessing the Receptor Selectivity a) Adenosine A1, A2a, A2b and A3 Receptor Selectivity Cells of the CHO (Chinese Hamster Ovary) permanent cell line are transfected stably with the cDNA for the adenosine receptor subtypes A1, A2a, A2b and A3. The binding of the substances to the A2a or A2b receptor subtypes is determined by measuring the intracellular cAMP content in these cells using a conventional radioimmunological assay (cAMP RIA).

When the substances act as agonists, the binding of the substances is expressed as an increase in the intracellular content of cAMP. The adenosine-analogous compound NECA (5-N-ethylcarboxamido-adenosine), which binds all adenosine receptor subtypes with high affinity but not selectively and possesses an agonistic effect, is used as the reference compound in these experiments (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1-9).

The adenosine receptors A1 and A3 are coupled to a Gi protein, i.e. stimulation of these receptors leads to inhibition of the adenylate cyclase and consequently to a lowering of the intracellular cAMP level. In order to identify A1/A3 receptor agonists, the adenylate cyclase is stimulated with forskolin. However, an additional stimulation of the A1/A3 receptors inhibits the adenylate cyclase, which means that A1/A3 receptor agonists can be detected by a comparatively low content of cAMP in the cell.

In order to detect an antagonistic effect on adenosine receptors, the recombinant cells which are transfected with the corresponding receptor are prestimulated with NECA and the effect of the substances on reducing the intracellular content of cAMP occasioned by this prestimulation is investigated. XAC (xanthine amine congener), which binds to all adenosine receptor subtypes with high affinity and possesses an antagonistic effect, is used as the reference compound in these experiments (Müiller, C. E., Stein, B., Adenosine receptor antagonists: structures and potential therapeutic applications, Current Pharmaceutical Design, 2 (1996) 501-530).

b) Adenosine A1, A2a, A2b Receptor Selectivity

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance test screening:

The stock cultures are grown, at 37° C. and under 5% $CO_2$, in DMEM/F12 medium containing 10% FCS (fetal calf serum) and in each case split 1:10 after 2-3 days. The test cultures are seeded in 384-well plates at a rate of from 1 000 to 3 000 cells per well and grown at 37° C. for approx. 48 hours. The medium is then replaced with a physiological sodium chloride solution (130 mM NaCl, 5 mM KCl, 2 mM $CaCl_2$, 20 mM HEPES, 1 mM $MgCl_2 \cdot 6H_2O$, 5 mM $NaHCO_3$, pH 7.4). The substances, which are dissolved in DMSO, are diluted 1:10 three times with this physiological sodium chloride solution and pipetted into the test cultures (maximum final concentration of DMSO in the test mixture: 0.5%). In this way, final substance concentrations of, for example, from 5 μM to 5 nM are obtained. 10 minutes later, forskolin is added to the A1 cells and all the cultures are subsequently incubated at 37° C. for 4 hours. After that, 35 μl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM $MgSO_4$, 15 mM DTT, pH 7.8) are added to the test cultures, the plates are shaken for approx. 1 minute and the luciferase activity is measured using a camera system.

B. WORKING EXAMPLES

Example 1

2-Amino-4-(4-hydroxyphenyl)-6-[(3-pyridinylmethyl)amino]-3,5-pyridine-dicarbonitrile trifluoroacetate

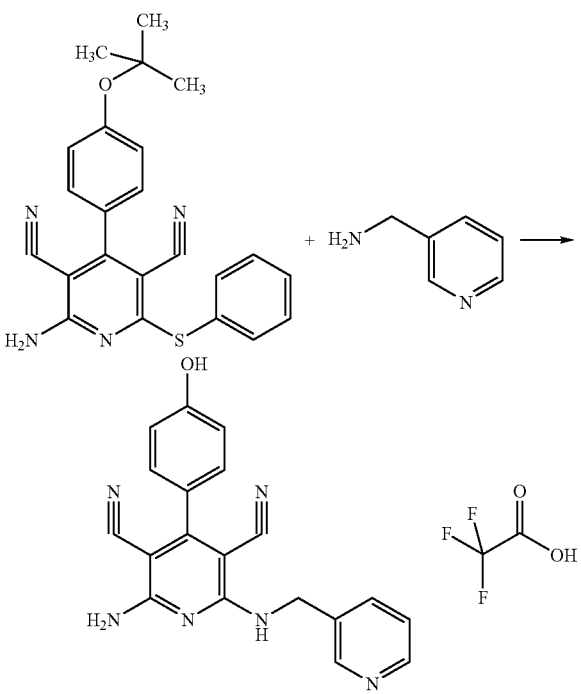

80.1 mg (0.2 mmol) of 2-amino-4-(4-tert-butoxyphenyl)-6-(phenylsulfanyl)-3,5-pyridinedicarbonitrile and 86 mg (0.8 mmol) of 3-picolylamine in 0.5 ml of dimethyl sulfoxide (DMSO) are shaken at 120° C. for 10 hours. The reaction solution is purified by preparative HPLC.

Column: Grom-sil 120 ODS-4 HE 5 μm 20×50 mm,
Precolumn: Grom-sil ODS-4 HE 15 μm 10×20 mm.
Flow rate: 25 ml/min.
Gradient (A=acetonitrile, B=water+0.3% trifluoroacetic acid):
0 min 10% A;
2.00 min 10% A;
6.00 min 90% A;
7.00 min 90% A;
7.10 min 10% A;
8 min 10% A.
Detection: 220 nm. Injection volume: 510 μl of DMSO sol.

The product fraction is concentrated under reduced pressure and dissolved in 0.7 ml of trifluoroacetic acid. After 30 min at RT, the mixture is concentrated under reduced pressure.

Yield: 31.3 mg (=45.7% of theory) of product

Mass spectrum: molar mass required: 342, found [M+H]$^+$= 343

Example 2

2-Amino-4-phenyl-6-[(3-pyridinylmethyl)amino]-3,5-pyridinedicarbonitrile trifluoroacetate

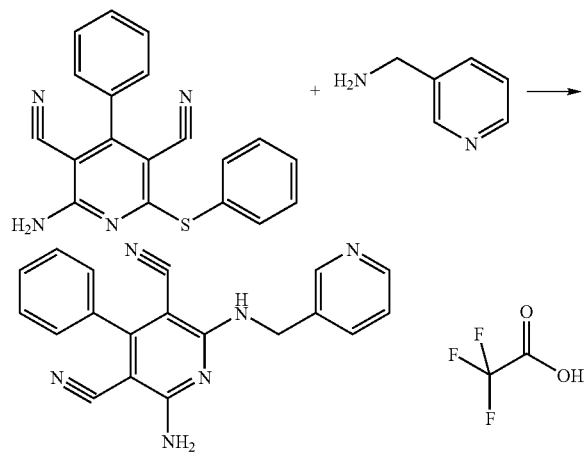

32.4 mg (0.1 mmol) of 2-amino-4-phenyl-6-(phenylsulfanyl)-3,5-pyridine-dicarbonitrile and 43 mg (0.4 mmol) of 3-picolylamine in 0.5 ml of DMSO are shaken at 120° C. for 18 hours. The reaction solution is purified by preparative HPLC.

Column: Grom-sil 120 ODS-4 HE 5 μm 20×50 mm,

Precolumrn: Grom-sil ODS-4 HE 15 μm 10×20 mm.

Flow rate: 25 ml/imin.

Gradient (A=acetonitrile, B=water+0.3% trifluoroacetic acid):

0 min 10% A;

2.00 min 10% A;

6.00 min 90% A;

7.00 min 90% A;

7.10 min 10% A;

8min 10%.

Detection: 220 nm. Injection volume: 510 μl of DMSO sol.

The product fraction is concentrated under reduced pressure.

Yield: 21.5 mg (=66% of theory) of product

Mass spectrum: molar mass required: 326, found [M+H]$^+$= 327

$^1$H-NMR spectrum [DMSO-d$_6$)]: δ=4.55 [2H] d; 7.3-7.55 [8H] m; 7.95 [1H] s broad; 8.1 [1H] s broad; 8.5 [1H] s; 8.7 [1H] s.

The compounds listed in the table below (Examples 3 to 40) are prepared analogously to the procedures of Examples 1 and 2 given above. The identity and purity of the compounds is detected by LC-MS.

| Ex. No. | Target structure | Molar mass required | Found [M + H]$^+$ | Yield (% of theory) |
|---|---|---|---|---|
| 3 | | 342 | 343 | 90 |
| 4 | | 341 | 342 | 66 |

-continued

| Ex. No. | Target structure | Molar mass required | Found [M + H]+ | Yield (% of theory) |
|---|---|---|---|---|
| 5 | | 381 | 382 | 62 |
| 6 | | 279 | 280 | 42 |
| 7 | | 307 | 308 | 60 |
| 8 | | 307 | 308 | 61 |
| 9 | | 343 | 344 | 47 |

-continued

| Ex. No. | Target structure | Molar mass required | Found [M + H]⁺ | Yield (% of theory) |
|---|---|---|---|---|
| 10 | | 383 | 384 | 78 |
| 11 | | 295 | 296 | 86 |
| 12 | | 356 | 357 | 86 |
| 13 | | 371 | 372 | 51 |

-continued

| Ex. No. | Target structure | Molar mass required | Found [M + H]+ | Yield (% of theory) |
|---|---|---|---|---|
| 14 | | 291 | 292 | 71 |
| 15 | | 293 | 294 | 87 |
| 16 | | 305 | 306 | 89 |
| 17 | | 356 | 357 | 99 |
| 18 | | 409 | 410 | 84 |

-continued

| Ex. No. | Target structure | Molar mass required | Found [M + H]⁺ | Yield (% of theory) |
|---|---|---|---|---|
| 19 | (structure) | 428 | 429 | 85 |
| 20 | (structure) | 409 | 410 | 74 |
| 21 | (structure) | 346 | 347 | 42 |
| 22 | (structure) | 362 | 363 | quantitative |
| 23 | (structure) | 342 | 343 | 77 |

-continued

| Ex. No. | Target structure | Molar mass required | Found [M + H]+ | Yield (% of theory) |
|---|---|---|---|---|
| 24 | | 342 | 343 | quantitative |
| 25 | | 363 | 364 | quantitative |
| 26 | | 362 | 363 | 87 |
| 27 | | 360 | 361 | 97 |
| 28 | | 340 | 341 | 68 |

-continued

| Ex. No. | Target structure | Molar mass required | Found [M + H]+ | Yield (% of theory) |
|---|---|---|---|---|
| 29 | | 340 | 341 | 82 |
| 30 | | 347 | 348 | 60 |
| 31 | | 355 | 356 | 67 |
| 32 | | 359 | 360 | 73 |
| 33 | | 359 | 360 | 85 |

-continued

| Ex. No. | Target structure | Molar mass required | Found [M + H]+ | Yield (% of theory) |
|---|---|---|---|---|
| 34 | | 373 | 374 | 72 |
| 35 | | 399 | 400 | 59 |
| 36 | | 390 | 391 | 22 |
| 37 | | 350 | 351 | 28 |
| 38 | | 388 | 389 | 87 |

| Ex. No. | Target structure | Molar mass required | Found [M + H]+ | Yield (% of theory) |
|---|---|---|---|---|
| 39 | 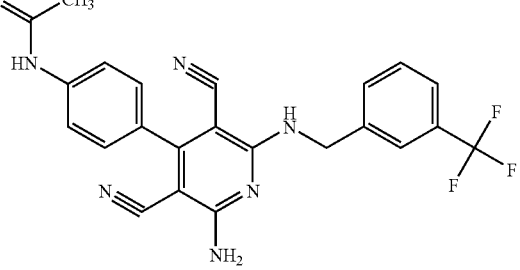 | 450 | 451 | quantitative |
| 40 | 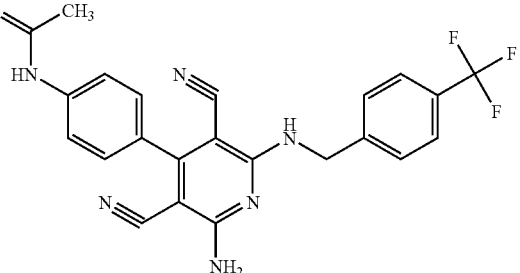 | 450 | 451 | 77 |

Example 3 shows the following ¹H-NMR-spectroscopic data:

¹H-NMR spectrum [DMSO-d₆]: δ=4.55 [2H] d; 6.8 [1H] s; 6.85 [1H] d; 6.9 [1H] d; 7.3 [1H] tr; 7.3-7.5 [2H] m broad; 7.95 [1H] s; 8.1 [1H] tr; 8.45 [1H] s; 8.8 [1H] s; 9.8 [1H] s broad.

Example 4 shows the following ¹H-NMR spectroscopic data:

¹H-NMR spectrum [DMSO-d₆]: δ=4.55 [2H] d; 6.8 [1H] s; 6.85 [1H] dd; 6.9 [1H] d; 7.2-7.45 [8H] m; 8.0 [1H] tr; 9.8 [1H] s.

Example 41

1ˢᵗ Step

2-Chloro-4-phenyl-6-(phenylsulfanyl)-3,5-pyridinedicarbonitrile

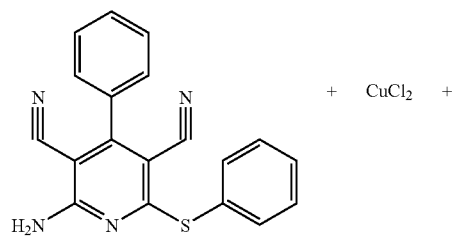 + CuCl₂ + 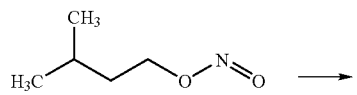 →

-continued

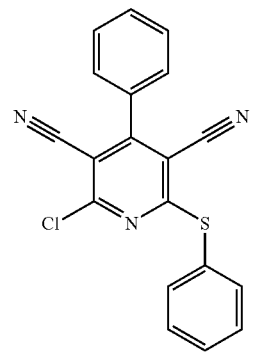

Under argon, 24.5 g (182 mmol) of anhydrous copper(II) chloride are suspended in 180 ml of acetonitrile, and 21.4 g (182 mmol) of isopentyl nitrite are then added dropwise. After 20 min of stirring at room temperature, 10 g (30.5 mmol) of 2-amino-4-phenyl-6-(phenylsulfanyl)-3,5-pyridinedicarbonitrile [Kambe et al., Synthesis, 531-533 (1981)] are added. The mixture is stirred at room temperature over the weekend. For work-up, 150 ml of 1 N hydrochloric acid are added to the mixture, the mixture is extracted 4× with dichloromethane and the organic phase is washed once with saturated sodium chloride solution, dried over magnesium sulfate and concentrated under reduced pressure. The residue is triturated with a little ethyl acetate and allowed to stand in a fridge for 1 hour. The crystals are filtered off with suction and washed with a little cold ethyl acetate and diethyl ether.

Yield: 7.26 g (68.5% of theory) of product

Mass spectrum: molar mass required: 347, found [M+H]$^+$= 348

2$^{nd}$ Step

2-[(2-Hydroxyethyl)amino]-4-phenyl-6-(phenylsulfanyl)-3,5-pyridinedicarbonitrile

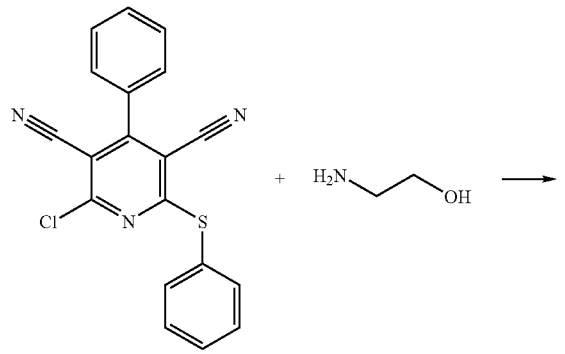

Under argon, 0.7 g (2 mmol) of 2-chloro-4-phenyl-6-(phenylsulfanyl)-3,5-pyridine-dicarbonitrile (1$^{st}$ step) is dissolved in 2 ml of dimethylformamide (DMF), 0.27 g (4.5 mmol) of 2-hydroxyethylamine is added and the mixture is stirred at room temperature for 15 minutes. After addition of 2 ml of methanol, about 1 ml of water is added dropwise and the precipitate is filtered off with suction. The crystals are purified by boiling with 4 ml of methanol.

Yield: 410 mg (=55% of theory) of product

Mass spectrum: molar mass required: 372, found [M+H]$^+$= 373

3$^{rd}$ Step

2-(Benzylamino)-6-[(2-hydroxyethyl)amino]-4-phenyl-3,5-pyridinedicarbonitrile

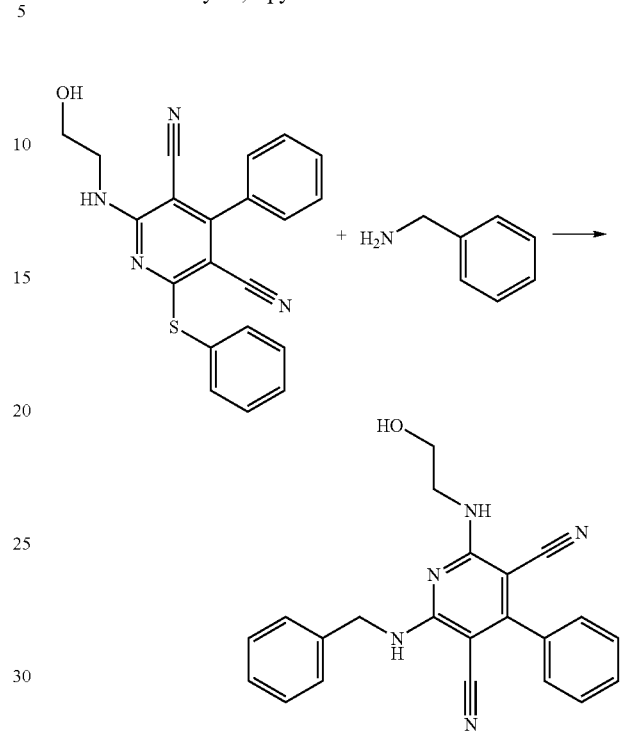

32.4 mg (0.1 mmol) of 2-[(2-hydroxyethyl)amino]-4-phenyl-6-(phenylsulfanyl)-3,5-pyridinedicarbonitrile (2$^{nd}$ step) and 43 mg (0.4 mmol) of benzylamine in 0.5 ml of dimethyl sulfoxide (DMSO) are shaken at 120° C. for 2 hours. The reaction solution is purified by preparative HPLC in two injections.

Column: Kromasil 100 C$_{18}$ 5 µm 20×50 mm,

Precolumn: Grom-sil ODS 4 HE 15 µm 10×20 mm.

Flow rate: 25 ml/min.

Gradient (A=acetonitrile, B=water+0.3% trifluoroacetic acid):

0 min 10% A;

2.00 min 10% A;

6.00 min 90% A;

7.00 min 90% A;

7.10 min 10% A;

8 min 10% A.

Detection: 220 nm. Injection volume: 300 µl of DMSO sol.

The product fraction is concentrated under reduced pressure.

Yield: 35.3 mg (=47.8% of theory) of product

Mass spectrum: molar mass required: 369, found [M+H]$^+$= 370

The compounds listed in the table below (Examples 42 to 59) are prepared analogously to the procedures of Example 41 given above. The identity and purity of the compounds is detected by LC-MS.

| Ex. No. | Target structure | Molar mass required | Found [M + H]+ | Yield (% of theory) |
|---|---|---|---|---|
| 42 | | 454 | 455 | 67 |
| 43 | | 468 | 469 | 54 |
| 44 | | 397 | 398 | 77 |
| 45 | | 411 | 412 | 70 |
| 46 | | 426 | 427 | 68 |

-continued

| Ex. No. | Target structure | Molar mass required | Found [M + H]+ | Yield (% of theory) |
|---|---|---|---|---|
| 47 | | 441 | 442 | 33 |
| 48 | | 402 | 403 | 48 |
| 49 | | 397 | 398 | 40 |
| 50 | | 411 | 412 | 55 |
| 51 | | 353 | 354 | 40 |

-continued
| Ex. No. | Target structure | Molar mass required | Found [M + H]+ | Yield (% of theory) |
|---|---|---|---|---|
| 52 | 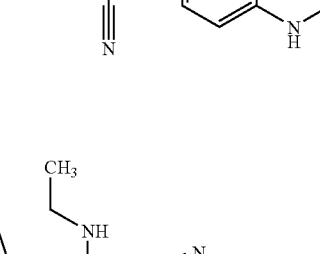 | 360 | 361 | 56 |
| 53 | 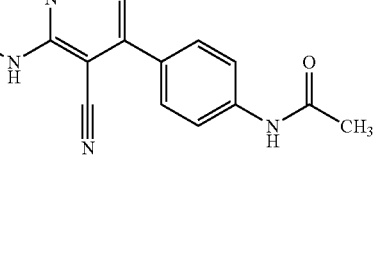 | 400 | 401 | 51 |
| 54 | 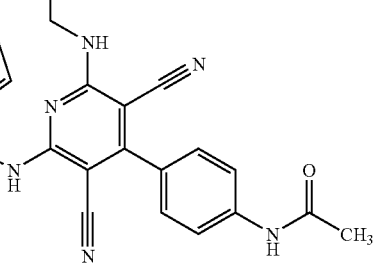 | 416 | 417 | 33 |
| 55 | 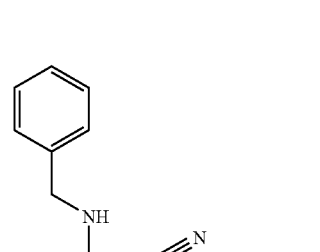 | 457 | 458 | 54 |

-continued

| Ex. No. | Target structure | Molar mass required | Found [M + H]+ | Yield (% of theory) |
|---|---|---|---|---|
| 56 | | 385 | 386 | 68 |
| 57 | | 431 | 432 | 99 |
| 58 | | 548 | 549 | 42 |
| 59 | | 395 | 396 | 46 |

Example 60

2-Amino-4-(2,3-dihydro-1,4-benzodioxin-6-yl)-6-[(3-pyridinylmethyl)amino]-3,5-pyridinedicarbonitrile

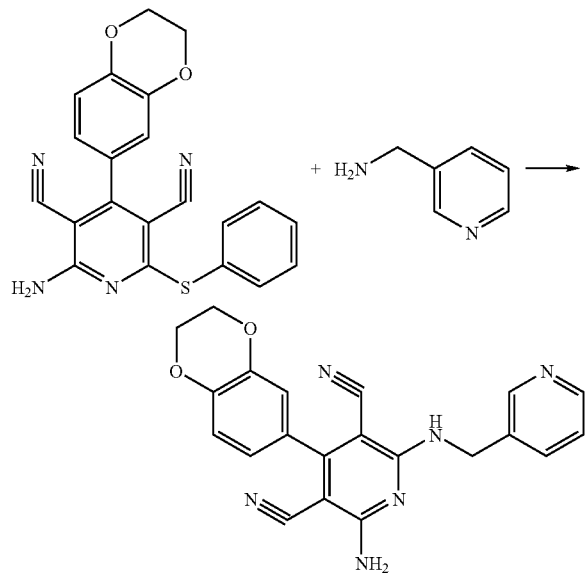

100 mg (0.26 mmol) of 2-amino-4-(2,3-dihydro-1,4-benzodioxin-6-yl)-6-(phenyl-sulfanyl)-3,5-pyridinedicarbonitrile and 56 mg (0.52 mmol) of 3-picolylamine in 8 ml of DMF are heated at 100° C. After 3 hours, another 224 mg (2.08 mmol) of 3-picolylamine are added, and the mixture is heated at 100° C. for another 4 hours. After dilution with water, the mixture is extracted three times with ethyl acetate. The combined organic phases are washed with saturated sodium chloride solution, dried over magnesium sulfate and concentrated. The concentration residue is purified by preparative HPLC on reversed-phase silica gel.

The product fraction is concentrated.

Yield: 31.3 mg (=31% of theory) of product

Mass spectrum: molar mass required: 384, found [M+H]$^+$= 385

$^1$H-NMR spectrum [DMSO-d$_6$]: δ=4.3 [4H] s; 4.55 [2H] d; 6.85-7.0 [3H] m; 7.3-7.55 [3H] m; 7.85 [1H] d; 8.1 [1H] tr; 8.45 [1H] d; 8.65 [1H] d.

Example 61

2-Amino-4-(2,3-dihydro-1,4-benzodioxin-6-yl)-6-[(2-pyridinylmethyl)amino]-3,5-pyridinedicarbonitrile

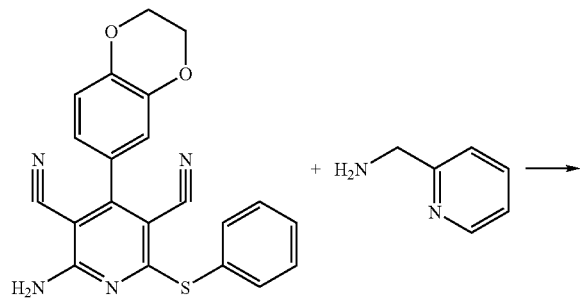

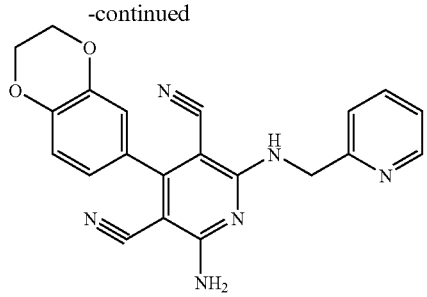

100 mg (0.26 mmol) of 2-amino-4-(2,3-dihydro-1,4-benzodioxin-6-yl)-6-(phenyl-sulfanyl)-3,5-pyridinedicarbonitrile and 56 mg (0.52 mmol) of 2-picolylamine in 8 ml of DMF are heated at 100° C. After 3 hours, another 224 mg (2.08 mmol) of 2-picolylamine are added, and the mixture is heated at 100° C. for another 4 hours. After dilution with water, the mixture is extracted three times with ethyl acetate. The combined organic phases are washed with saturated sodium chloride solution, dried over magnesium sulfate and concentrated. The evaporation residue is purified by preparative HPLC on reversed-phase silica gel.

The product fraction is concentrated and repurified by preparative thin-layer chromatography (mobile phase toluene/ethyl acetate 1:1).

Yield: 2 mg (=2% of theory) of product

Mass spectrum: molar mass required: 384, found [M+H]$^+$= 385

$^1$H-NMR spectrum [DMSO-d$_6$]: δ=4.3 [4H] s; 4.7 [2H] d; 6.9-7.0 [3H] m; 7.2-7.4 [4H] m; 7.75 [1H] tr; 7.9 [1H] tr; 8.5 [1H] d.

Example 62

2-Amino-4-(2,3-dihydro-1,4-benzodioxin-6-yl)-6-{[(2-methyl-1,3-thiazol-4-yl-methyl]amino}-3,5-pyridinedicarbonitrile

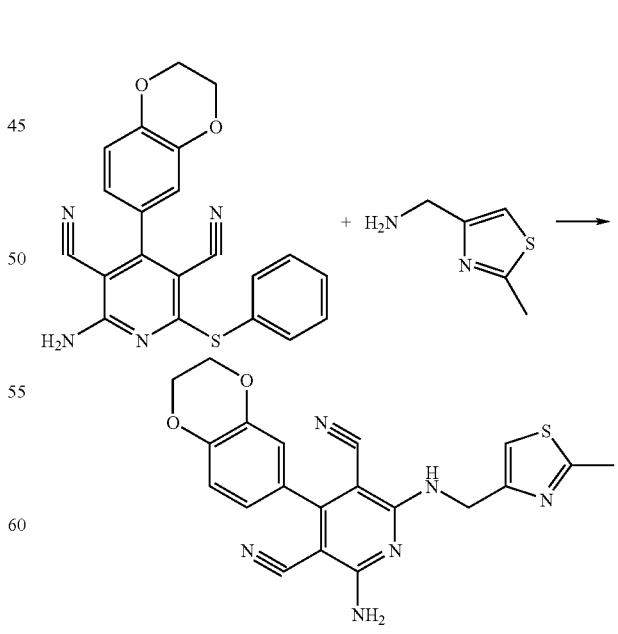

100 mg (0.26 mmol) of 2-amino-4-(2,3-dihydro-1,4-benzodioxin-6-yl)-6-(phenyl-sulfanyl)-3,5-pyridinedicarbonitrile and 66 mg (0.52 mmol) of (2-methyl-1,3-thiazolyl-4-yl)methylamine in 8 ml of 1,2-dimethoxyethane are heated at 90° C. After 2.5 hours, another about 500 mg (about 3.9 mmol) of (2-methyl-1,3-thiazol-4-yl)methylamine are added, and the mixture is heated at 90° C. for another 24 hours. The reaction mixture is concentrated and the evaporation residue is purified by preparative HPLC on reversed-phase silica gel.

The product fraction was concentrated.

Yield: 60 mg (=52% of theory) of product

Mass spectrum: molar mass required: 404, found [M+H]$^+$= 405

$^1$H-NMR spectrum [DMSO-d$_6$]: δ=2.65 [3H] s; 4.3 [4H] s; 4.65 [2H] s; 7.0 [3H] m; 7.3 [1H] s; 7.4 [2H] s; 7.4 [2H] s broad; 7.9 [1H] s broad.

The invention claimed is:

1. A compound of formula (I):

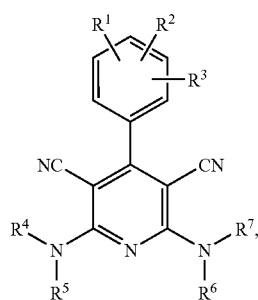

(I)

in which

R$^1$ represents hydrogen, hydroxyl, chlorine, nitro, methyl, methoxy, ethoxy, n-propoxy, isopropoxy, n-butoxy or —NH—C(O)—CH$_3$, where the alkoxy radicals for their part may be substituted by hydroxyl, methoxy, ethoxy, n-propoxy, isopropoxy, n-butoxy, —O—C(O)—CH$_3$ or cyclopropyl, R$^2$ and R$^3$ represent hydrogen, R$^4$ represents hydrogen, methyl, ethyl, n-propyl or isopropyl, where the alkyl radicals for their part may be substituted by pyridyl, methoxy, ethoxy, n-propoxy, isopropoxy, n-butoxy or mono- or disubstituted by hydroxyl, R$^5$ represents hydrogen, R$^6$ represents methyl, ethyl n-propyl, isopropyl, where the alkyl radicals for their part may be mono- or disubstituted, independently of one another, by cyclopropyl, pyridyl, furyl, thienyl, benzimidazolyl, pyrrolidinonyl, N-methylpyrrolidinonyl, N-methylpyrrolidinyl, N-ethylpyrrolidinyl, N-methylimidazolidinonyl, or cyclopropyl and R$^7$ represents hydrogen or a salt thereof.

2. A process for preparing the compound of claim 1 characterized in that a compound of the formula (II)

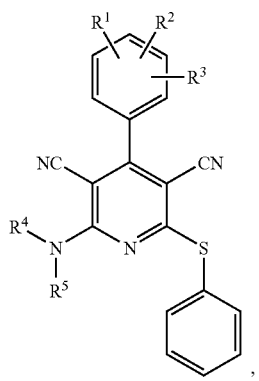

(II)

in which

R$^1$, R$^2$, R$^3$, R$^4$ and R$^5$ are as defined in claim 1, is reacted in a solvent with a compound of the formula (III)

R$^6$—NH—R$^7$ (III)

in which

R$^6$ and R$^7$ are as defined in claim 1.

3. A pharmaceutical composition, comprising at least one compound of the formula (I) as defined in claim 1 and at least one further auxiliary.

4. The compound of claim 1, wherein

R$^1$ represents hydrogen, hydroxyl, chlorine, nitro, methyl, methoxy, ethoxy, n-propoxy, isopropoxy, n-butoxy, or NH—C(O)—CH$_3$, where the alkoxy radicals for their part may be substituted by hydroxyl, or —O—C(O)—CH$_3$ or cyclopropyl, R$^2$ and R$^3$ represent hydrogen, R$^4$ represents hydrogen, methyl, ethyl, n-propyl or isopropyl, where the alkyl radicals for their part may be monosubstituted by hydroxyl, R$^5$ represents hydrogen, R$^6$ represents methyl, ethyl n-propyl, isopropyl, where the alkyl radicals for their part may be mono- or disubstituted, independently of one another, by cyclopropyl, pyridyl, furyl, thienyl, benzimidazolyl, pyrrolidinonyl, N-methylpyrrolidinonyl, N-methylpyrrolidinyl, N-ethylpyrrolidinyl, N-methylimidazolidinonyl, or cyclopropyl and R$^7$ represents hydrogen or a salt thereof.

5. The compound of claim 4, wherein the compound is

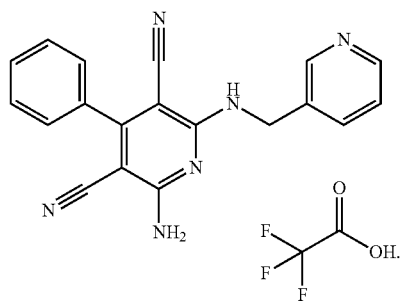

* * * * *